United States Patent [19]

Jones et al.

[11] 4,250,890

[45] Feb. 17, 1981

[54] PULMONARY ANALYZER

[75] Inventors: William C. Jones, Oak Brook; Clifford Harwood, Wheaton, both of Ill.

[73] Assignee: Jones Medical Instrument Company, Oak Brook, Ill.

[21] Appl. No.: 14,423

[22] Filed: Feb. 23, 1979

[51] Int. Cl.³ .............................................. A61B 5/08
[52] U.S. Cl. ................................. 128/728; 73/861.08
[58] Field of Search ....................... 128/716, 718–720, 128/724–729, 731, 732, 733; 73/194 E, 195

[56] References Cited

U.S. PATENT DOCUMENTS

| | | | |
|---|---|---|---|
| 3,771,512 | 11/1973 | Jones et al. | 128/723 |
| 3,905,355 | 9/1975 | Brudny | 128/733 |
| 3,977,394 | 8/1976 | Jones et al. | 128/728 |
| 3,991,304 | 11/1976 | Hillsman | 128/725 X |
| 4,034,743 | 7/1977 | Greenwood et al. | 128/725 |
| 4,092,981 | 6/1978 | Ertl | 128/731 |
| 4,116,228 | 9/1978 | Hudspeth et al. | 128/724 |

OTHER PUBLICATIONS

Hilberman et al, "On-Line Assessment ... ill", JAAMI, vol. 6, No. 1, Jan.-Feb. 1972.

*Primary Examiner*—Lee S. Cohen
*Attorney, Agent, or Firm*—Tilton, Fallon, Lungmus & Chestnut

[57] ABSTRACT

A self-contained, portable system for measuring and computing respiratory parameters of a test subject undergoing forced expired breathing maneuvers according to instructions including a spirometer for receiving the exhaled breath of the subject for generating a measurement signal, a miniaturized digital computer for receiving the measurement signal, a visual display for presenting alpha-numeric characters under control of the computer to generate indicia representative of the computed parameter results, the computer further including a central processing unit and a voltage control oscillator interconnected between the central processing unit and the spirometer for receiving the measurement signal from the spirometer and converting the same to digital signals for averaging by the central processing unit to substantially eliminate random noise.

6 Claims, 3 Drawing Figures

PULMONARY ANALYZER

This invention relates to a pulmonary analyzer and more particularly, an improvement upon our prior patents for computerized pulmonary analyzers U.S. Pat. Nos. 3,977,394 and 3,771,512.

There we disclosed a system using the electrical signal generated by a spirometer to measure and store test data for certain pulmonary functions. The analyzer included a programmable digital computer for analyzing the stored test data and comparing it with standardized predicted values, which were then printed.

The instant invention simplifies analysis of the pulmonary functions by focusing on the most widely required tests, the Forced Vital Capacity and the Maximum Voluntary Ventilation, thereby attaining maximal useful data with minimal cost expenditures. The results of these tests are visually displayed and compared with standardized results instantaneously upon test completion. The Forced Vital Capacity test measures the amount and rate of exhaling by a subject after inspiring all possible air into his lungs. The test results may be used to derive the following single force expiratory breathing maneuver measurements: the Forced Vital Capacity (FVC), the first second Forced Expiratory Volume ($FEV_1$), the ratio of the Forced Expiratory Volume to Forced Vital Capacity ($FEV_1/FVC$) and the mid-range Forced Expiratory Flow ($FEF_{25-75\%}$). These measurements may also be displayed and compared to standardized results. Maximal Voluntary Ventilation (MVV) measures the volume and rate of the subject's breathing in and out as fast and as deeply as possible for 10 to 15 seconds. These measurements are the most useful data for office, industrial health and general screening—but their accuracy is important.

According to the prior art as represented by our above-identified patents, a microminiaturized digital computer received the measurement signal and stored the same while retrieving previously stored respiratory parameters according to the physical characteristics of the subject and thereafter compared the same. This same approach is utilized in the instant invention but with certain advantageous differences for optimizing accuracy and miniaturization. Among the differences providing the foregoing advantages are a simplified interface between the spirometer and the Central Processing Unit whereby both random and harmonic noise are economically and substantially eliminated in the analog to digital signal conversion; a sub-system for efficiently presenting a visual display of the test results, predicted results and relationship therebetween; and means for developing the extrapolated zero based upon maximum flow rate in accordance with currently approved practice.

Other objects and advantages of the invention may be seen in the details of the ensuing specification.

The invention is explained in conjunction with the accompanying drawing, in which FIG. 1 is a perspective view of a device constructed in accordance with the teachings of the invention;

Figure 1:
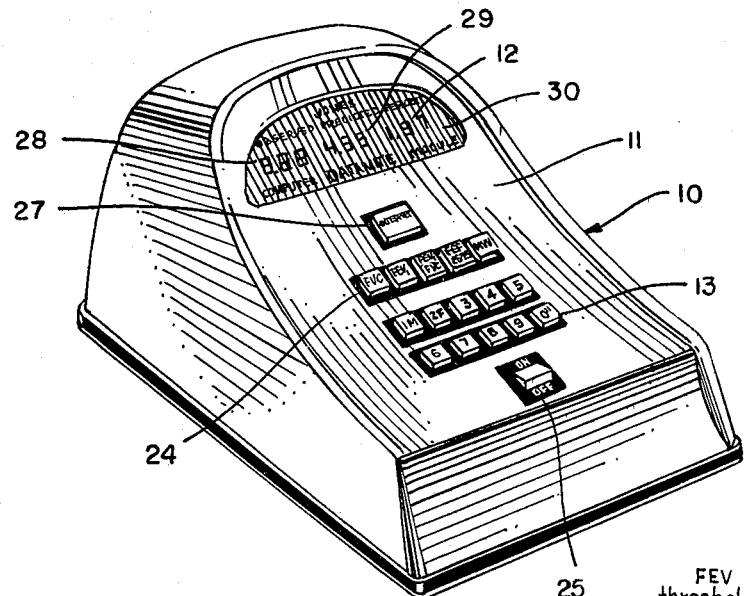

In the illustration given and with reference first to FIG. 1, the numeral 10 designates generally the inventive device which includes a housing 11 presenting a 9 digit, light-emitting diode display 12. Projecting from suitable apertures in the housing 11 are a plurality of keys 13 constituting a keyboard for use by an operator to introduce instructions for the testing. Generally, the operation and programming applicable here is analogous to that used in the above identified U.S. Pat. No. 3,977,394 and reference may be made thereto for additional details of construction and operation.

Figure 2:
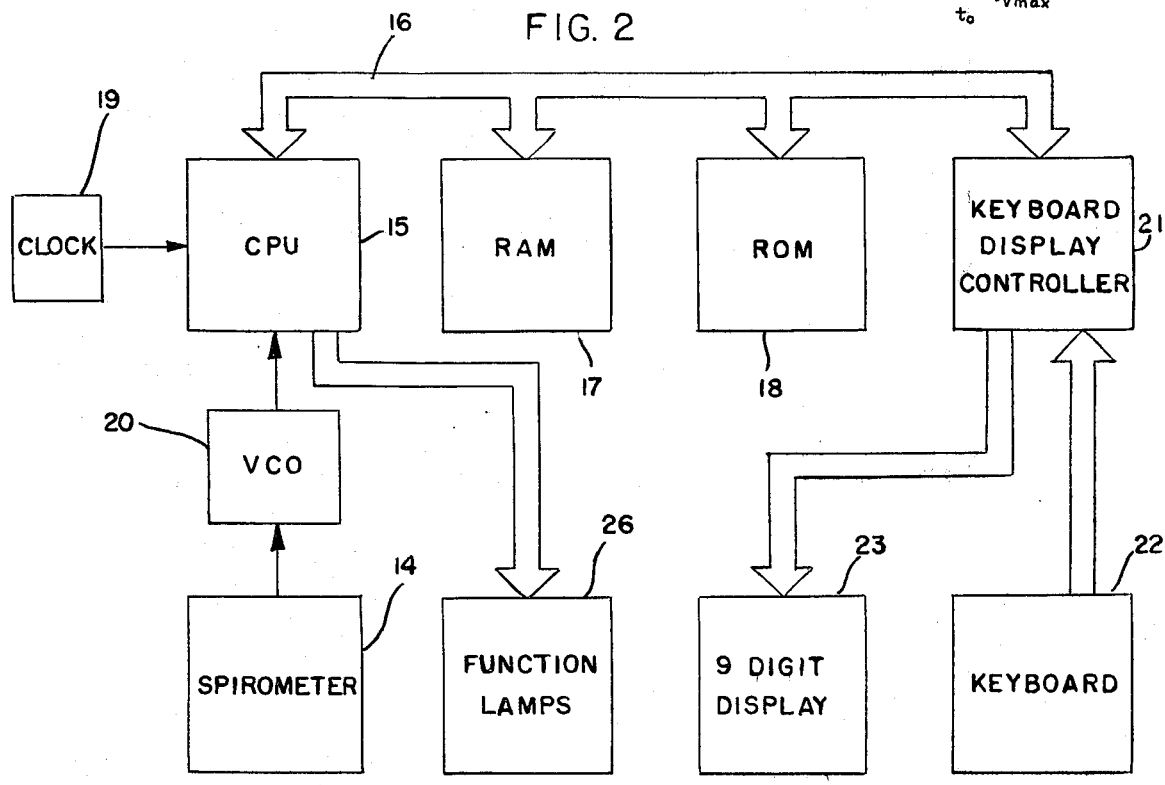
FIG. 2 is a functional block diagram of the analyzer of the invention.

Provided on the rear of the unit is a jack (hidden in FIG. 1) which receives the varying voltage signal from a spirometer 14 (see FIG. 2). The remainder of the elements in the block diagram of FIG. 2 are provided within the housing 11.

As pointed out previously, an advantageous difference between the analyzer of the instant invention and that of the prior art U.S. Pat. No. 3,977,394 is the manner in which the Varying Voltage Signal from the spirometer 14 is delivered to the Central Processing Unit 15. Also, as before, the CPU 15 is connected via a common Bus 16 with a Random Access Memory 17 and a Read Only Memory 18. Further, the CPU has associated therewith the usual clock 19.

Interposed between the spirometer 14 and the CPU 15 is a voltage controlled oscillator 20. The VCO 20 receives a voltage varying signal from the spirometer 14 and converts the signal into a series of pulses, i.e., a digital signal, proportional to the Voltage Varying Signal. The pulses are then transmitted to the CPU 15 for storage and subsequent analysis. Use of the VCO 20 limits the number of digital signals required and thereby reduces the amount of hardware required for analog-to-digital conversion. In addition, the VCO 20 serves to eliminate random noise coming from the spirometer potentiometer and other mechanical devices associated with the spirometer 14.

The CPU 15, in the illustration given, measures the pulse rate by averaging the digitized information presented thereto from the VCO 20. In addition, the CPU performs an additional important function relative to noise by eliminating therefrom objectionable 60 Herz noise as well as the harmonics thereof. This comb filtering is achieved through a computation process in the CPU 15 and the ROM 18 which includes multiplications, additions, delays and storage functions, thus supplementing the elimination of random noise achieved via averaging. Thus, for all practical purposes, the CPU 15 is organized to filter digital signals above about 30 Herz. Comb filtering is described in detail in the publication Electronics for July 24, 1967 at pages 91–100.

Another advantageous difference from the prior art analyzer illustrated by U.S. Pat. No. 3,977,394 is the provision of a keyboard display controller 21 which is interposed between the CPU 15 on the one hand and the keyboard 22 and the 9 digit display 23 on the other hand. By separating the logic having to do with the keyboard and what previously constituted the printout a significant simplifiation is achieved in the CPU 15 while simultaneously providing an advantageous display refreshment and renewing the display at 90 Herz so as to avoid objectionable eye flicker. The keyboard display controller 21, like the CPU 15, is a microprocessor chip similar to the type employed in U.S. Pat. No. 3,977,394. A keyboard display controller is described in the INTEL manual MCS-48 of 1977, under Publication No. 98-270B.

In the operation of the invention, the analyzer 10 is connected to a source of electricity which is converted to 5 Volts DC by a power pack (not shown) provided within the housing 11. After the on-off button 25 is pressed to initiate the test and the age, height and sex of the subject keyed on the numeric buttons 13, one of the function buttons 24 is depressed for selection of the particular test, and/or display of particular test results. These buttons are constructed of translucent plastic and are equipped with lamps generally designated function lamps 26 under the control of the CPU 15. Another button 27 is designated "INTERPRET" which provides a numeric coded display of test results as overview descriptive statemens. The 9 digits reflect the observed results as found at 28, the predicted results at 29 stemming from the information introduced into the RAM 17 by the operator and the percentage relationship as at 30.

Figure 3:
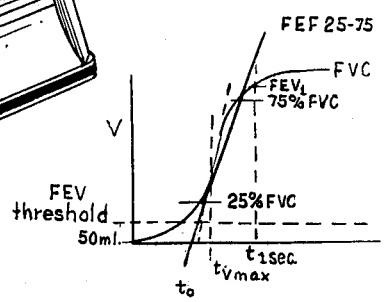
FIG. 3 is a graph plotting volume versus time of exhalation to determine the beginning of exhalation.

The maximum flow rate is recorded once the preliminary FEV threshold has been exceeded. In FIG. 3 this occurs on the FVC curve at $t_{\dot{v}max}$ above the horizontal threshold where the slope, a measure of volume over time, is the greatest. The "zero" starting point for exhalation may then be determined using a preprogrammed, mathematical process in ROM 18 to extrapolate the slope to intercept the abscissa—thereby establishing a point of starting exhalation which is readily recognized and duplicatable for comparison purposes.

While in the foregoing specification, a detailed description of the invention has been set down for the purpose of illustration, many variations in the details hereingiven may be made by those skilled in the art without departing from the spirit and scope of the invention.

We claim:

1. A self-contained, portable system for measuring and computing respiratory parameters of a test subject undergoing forced expired breathing maneuvers according to instructions, comprising: transducer means including spirometer means receiving the exhaled breath of the subject for generating a measurement signal representative of the volume of gas exhaled by said subject during a predetermined forced breathing maneuver; miniaturized digital computer means including clock circuit means for generating timing signals, said computer means receiving said measurement signal for acquiring and storing digital signals representing a stored record of said forced maneuver, in timed relation with said timing signals and for computing predetermined respiratory parameters of said subject from said stored signals; keyboard means comprising a plurality of digit key means selectively actuatable by an operator and communicating with said computer means for entering data relating to said particular subject, and a plurality of function key means for controlling the acquisition of a record of a forced breathing maneuver from said spirometer means in timed relation with said timing signals and for communicating with said computer means for controlling the sequence of operation and computation of said system; and visual display means for presenting alphanumeric characters under control of said computer means to generate indicia representative of the computed parameter results selected by the operator through said keyboard means, said computer means further including a central processing unit and a voltage controlled oscillator interconnected between said central processing unit and said transducer means, said voltage controlled oscillator receiving said measurement signal from said transducer means and converting the same to digital signals for averaging by said central processing unit to substantially eliminate random noise.

2. The system of claim 1 in which said spirometer means includes means for generating a varying voltage signal as said measurement signal, said voltage controlled oscillator being equipped with means for converting said varying voltage signal to a pulse train the frequency of which is proportional to said varying voltage signal.

3. The system of claim 1 in which said computer means includes a read only memory connected to said central processing unit, said read only memory having means including sequencing logic for filtering signals of 60 Herz and harmonics thereof whereby said digital signals are storable substantially free of both random and 60 Herz harmonic noise.

4. The system of claim 3 in which said sequencing logic includes a comb filter.

5. The system of claim 1 in which said computer means includes a keyboard display controller separate from but responsive to said central processing unit, said visual display means including a lamp display under the control of said keyboard display controller.

6. The system of claim 1 in which said computer means includes a read only memory programmed to report a start of exhalation based upon extrapolating the point of maximum slope of the time-volume curve to intersect the abscissa thereof.

* * * * *